(12) United States Patent
Farin et al.

(10) Patent No.: US 6,428,507 B1
(45) Date of Patent: *Aug. 6, 2002

(54) METHOD AND DEVICE FOR RINSING

(75) Inventors: Günther Farin, Tübingen; Klaus Fischer, Nagold; Karl Ernst Grund, Tübingen; Helmut Wurster, Oberderdingen, all of (DE)

(73) Assignee: Erbe Elektromedizin GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/068,665

(22) PCT Filed: Nov. 8, 1996

(86) PCT No.: PCT/EP96/04905
§ 371 (c)(1),
(2), (4) Date: Oct. 19, 1998

(87) PCT Pub. No.: WO97/17010
PCT Pub. Date: May 15, 1997

(30) Foreign Application Priority Data

Nov. 10, 1995 (DE) .......................... 195 42 020
Dec. 6, 1995 (DE) .......................... 195 45 528

(51) Int. Cl.$^7$ .............................. A61M 1/00
(52) U.S. Cl. ............... 604/118; 604/140; 600/158; 600/156
(58) Field of Search .......................... 604/48, 507, 514, 604/515, 73, 93, 118, 119, 120, 140, 146, 147, 149, 247, 290, 289, 93.01, 902, 141, 30, 32, 33–35, 121, 123, 22; 600/158, 156, 159

(56) References Cited

U.S. PATENT DOCUMENTS

| | | | | |
|---|---|---|---|---|
| 4,550,716 A | * | 11/1985 | Kinoshita | 128/6 |
| 4,552,130 A | * | 11/1985 | Kinoshita | 128/4 |
| 4,760,838 A | * | 8/1988 | Fukuda | 128/4 |
| 4,800,869 A | * | 1/1989 | Nakajima | 128/4 |
| 4,844,052 A | * | 7/1989 | Iwakoshi et al. | 128/4 |
| 5,027,791 A | * | 7/1991 | Takahashi | 128/4 |
| 5,191,878 A | * | 3/1993 | Iida et al. | 128/4 |
| 5,520,667 A | * | 5/1996 | Roche | 604/290 |
| 5,562,692 A | * | 10/1996 | Bair | 606/167 |
| 5,591,184 A | * | 1/1997 | McDonnell et al. | 606/167 |
| 5,702,384 A | * | 12/1997 | Umeyama et al. | 604/892.1 |

* cited by examiner

*Primary Examiner*—Brian L. Casler
*Assistant Examiner*—Cris Rodriguez
(74) *Attorney, Agent, or Firm*—St. Onge Steward Johnston & Reens LLC

(57) ABSTRACT

A method for rinsing a field of inspection or operation during an endoscopic procedure includes filling a proximal portion of a conduit with a fluid quantity defining a slug of liquid and accelerating the slug of liquid using gas which is fed into the conduit upstream of the fluid quantity, so as to have the slug of liquid discharged from the conduit at a high speed.

6 Claims, 2 Drawing Sheets

METHOD AND DEVICE FOR RINSING

DESCRIPTION

This application is a 371 of PCT/EP96/04905 filed on Nov. 8, 1996 under the International Convention and based on German Applications DE19542020.9 filed on Nov. 10, 1995, and DE 195 45528.2 filed on Dec. 6, 1995.

The invention relates to a method and an apparatus for rinsing a region to be treated or an operation field during endoscopy.

BACKGROUND OF THE INVENTION

During endoscopy, i.e. the examination of body cavities by means of an endoscope or a surgical operation employing an endoscope, it often happens that the area being viewed or operation area must be freed of debris in order to obtain a clear field of view or to clean the actual site of the operation. Especially when the material to be removed is very solid or firmly attached to the wall of the body cavity, it is difficult to expose the regions of interest.

Rinsing devices to rinse or clean a region to be treated or operation field are known, by means of which a rinsing fluid can be applied to the region or field to be rinsed or cleaned by passing the fluid at an adjustable flow rate through a rinsing or instrument channel of an endoscope. However, it is a disadvantage of these rinsing devices that in order to remove solid materials or those firmly adhering to the wall of the organ, a large amount of rinsing fluid must be introduced into the body cavity or hollow organ concerned.

The German patent DE 40 00 410 A1 discloses an endoscope comprising a rinsing device that enables application of an air-liquid mixture through an instrument channel of the endoscope.

For this purpose the said rinsing device incorporates a pump aggregate equipped with both a water pump and an air pump, which can be activated simultaneously or in alternation, either automatically or by operating a switch, so that an air-liquid mixture is passed through the instrument channel into the treatment region or onto the operation field. The air and liquid are brought together within the pump aggregate, in a connecting piece, from which the mixture passes through a single, common tube to a bifurcation at the proximal end of the instrument channel, even when both a water pump and an air pump are attached to the connecting piece.

In comparison to the rinsing devices mentioned above, this rinsing device offers the advantage that less water is introduced into the body cavity or into the organ to be treated; however, it is still not sufficiently effective in removing solid materials or those firmly adhering to the organ wall. The degree to which its efficacy can be increased by raising the pressure of the air-liquid mixture is restricted by the limited pressure resistance of the instrument channels of flexible endoscopes.

SUMMARY OF THE INVENTION

The object of the invention is to provide an improved cleaning action in a simple manner, with a reduced amount of liquid and the lowest possible pressure.

This object is achieved according to the method and apparatus of the invention.

It is an essential point of the invention that the cleaning liquid is not, continuously applied, as is known from the prior art, but is supplied toward an examining area in a controlled manner providing a series of separate fluid portions each of which is driven at an accelerated rate by a following gas portion. The energy of such a fluid portion is determined to a greater extent by its velocity, and this velocity in turn can be adjusted within a wide range by the gas pressure and the distance over which the individual projectile-like "slug" of liquid travels (which is available to a greater extent especially in very long endoscopes). The amount of liquid thus introduced is correspondingly small and, in addition, can therefore be very easily adjusted, because the adjustment is applied to individual (small) amounts of liquid. A further advantage is that the system can operate with a relatively low pressure (high pressure could endanger the patient and exceed the resistance of the working channel of an endoscope), because the energy of the individual liquid slugs increases progressively over the (long) travel distance, until at the exit opening (in some cases the opening of the endoscope channel) it has substantially reached its maximum.

Preferably a plurality of liquid slugs are ejected in succession, in particular at regular intervals; the pauses between the slugs should not be too short, in order to operate with minimal amounts of fluid and to enable the cleaning process to be stopped immediately, as soon as the desired result has been achieved. It is preferable in this regard for the amount of liquid in each slug (projectile), the pressure of the gas that accelerates the slug, and the intervals at which the slugs leave the opening of the tube all to be adjustable.

In a preferred embodiment of the invention controllable valves are provided, by means of which the tube can be connected in alternation with a source of liquid and a source of compressed gas. This arrangement optimizes controllability. In a particularly simple embodiment of the invention the proximal section of the tube is connected to a liquid source that is under a first pressure by way of a valve that permits flow only in the direction toward the opening of the tube, and is also connected to a compressed-gas source, the pressure of which alternates in time between levels above and below the first pressure. As a result, whenever the gas pressure falls below the liquid pressure, a slug of liquid enters the tube, and when the gas pressure again rises above the liquid pressure, the slug is accelerated and ejected.

BRIEF DESCRIPTION OF THE DRAWINGS

Preferred embodiments of the invention will become apparent from the subordinate claims and the following description of exemplary embodiments with reference to figures, wherein

DETAILED DESCRIPTION OF THE INVENTION

Figure 1:
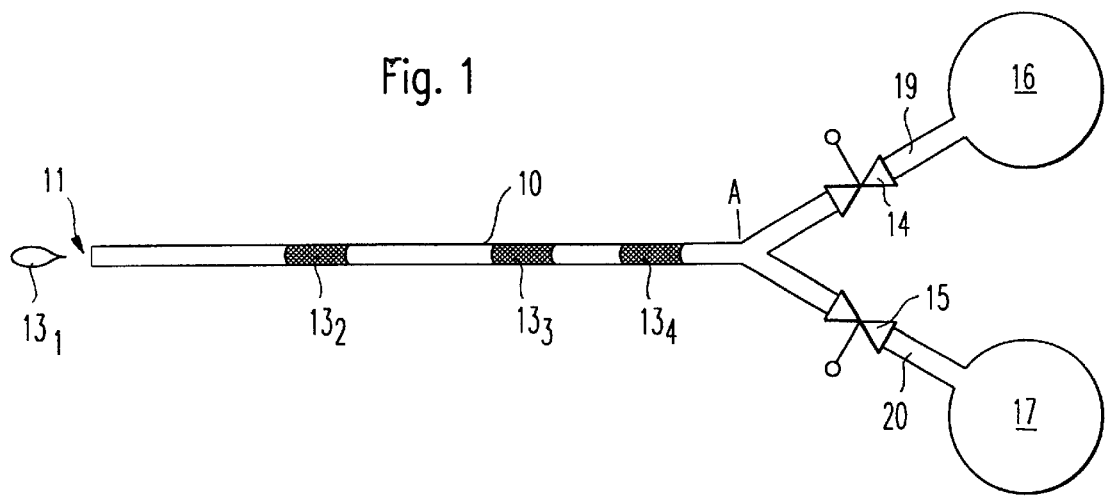
FIG. 1 is a schematic drawing of the invention with two valves.

In the following description, the same parts or parts with similar actions are indicated by the same reference numerals.

The highly schematic arrangement shown in FIG. 1 comprises a conduit 10, which can be the working channel of an endoscope or a tube or pipe inserted into that channel. The conduit 10 is connected to a compressed-gas source 16 (a pump or gas cylinder or gas main) by way of a first connecting pipe 19, and to a liquid source 17 by way of a second connecting pipe 20. The junction of the two connecting pipes is labelled "A" and is positioned so close to the endoscope, or to the opening 11 of the conduit 10, that the "exit velocity" (explained further below) that is reached is substantially maximal. The outlets of the valves (in particular the gas valve 14) are positioned as close as possible to the junction A, in particular at the proximal end of the working channel of the endoscope. The first connecting pipe 19 can be closed off by a first controllable valve 14 and the second connecting pipe 20, by a second controllable valve 15. The function of the system is described in the following, the opened and closed states of the valves 14, 15 being denoted in FIG. 2 by "1" for opened and "0" for closed. The upper time course, labelled "a", shows the operation of the valve 14, while the lower time course, labelled "b", shows the operation of the valve 15. At a first time $t_0$, the second valve 15 opens; it remains open for a specified period $T_1$, and thus closes at the time $t_0+T_1$. During the open period a particular amount of liquid passes out of the liquid source 17 into the conduit 10, where it forms a "slug" 13.

Figure 2:
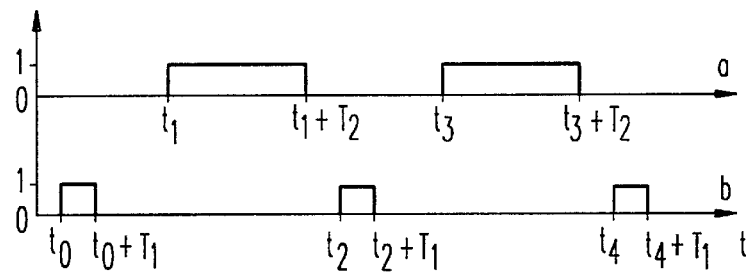
FIG. 2 is a time diagram to explain the action of the arrangement and control of the valves.

At a time $t_1$ after the time $t_0+T_1$, the first valve 14 is opened, so that the compressed-gas source 16 communicates with the conduit 10. The duration of opening is indicated in FIG. 2 by $T_2$. The gas, under pressure, accelerates the liquid slug 13, which moves toward the opening 11 of the conduit 10. After the valve 14 has closed, the process just described begins anew at a time $t_2$, at which the valve 15 opens for the predetermined period $T_1$. That is, liquid slugs $13_1$, $13_2$, $13_3$ and $13_4$ are introduced into the conduit 10 and accelerated by compressed gas from the source 16 in succession, so that they emerge like projectiles from the opening 11 and strike the surface to be cleaned (not shown). The gas cushion that accelerates each slug should at this time (emergence from the opening) have reached the ambient pressure, while the slug should have reached its maximal velocity (energy).

Figure 3:
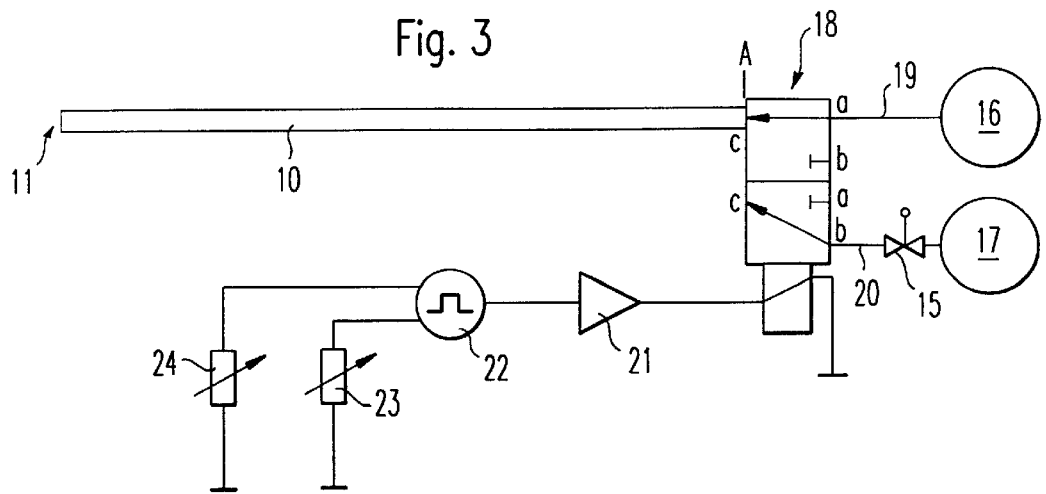
FIG. 3 shows a further embodiment of the invention, with a 3-way valve.

The embodiment of the invention shown in FIG. 3 differs from that according to FIG. 1 in that the system is provided not with two separate valves 14 and 15 but rather with a 3-way valve 18, the two inputs a and b of which are connected, respectively, to the compressed-gas source 16 by way of pipe 19 and to the liquid source 17 by way of pipe 20, and the output c of which communicates with the conduit 10. The 3-way valve 18 is controlled by way of an amplifier 21, the input of which is connected to the output of a controller 22 that drives the valve 18 at a frequency determined by a first adjustment unit 23 and with a pulse duration that can be set by a second adjustment unit 24. Here, again, in the second connecting pipe 20 a second valve 15 is provided, which is open when the arrangement is operating and closed when operation is halted; in the latter situation, the 3-way valve 18 remains in the position b–c. In its function the arrangement according to FIG. 3 differs from that shown by the diagram in FIG. 2 in that between the times $t_0+T_1$ and $t_1$, as well as between $t_1+T_2$ and $t_2$ (and so on), there are only very slight pauses, determined by the time needed for switching of the 3-way valve 18.

Figure 4:
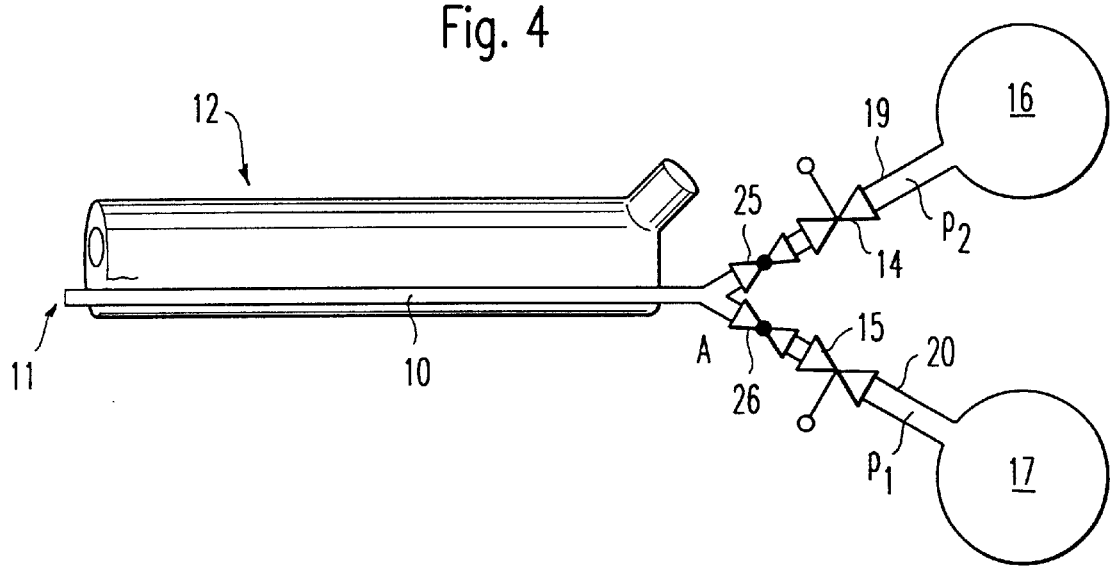
FIG. 4 shows a further embodiment of the invention, with pulsating compressed-gas source.

In FIG. 4 another embodiment of the invention is shown schematically. This again comprises a conduit 10, which is pushed through the working channel of an endoscope 12 in such a way that its opening 11 projects out of the endoscope.

Figure 5:
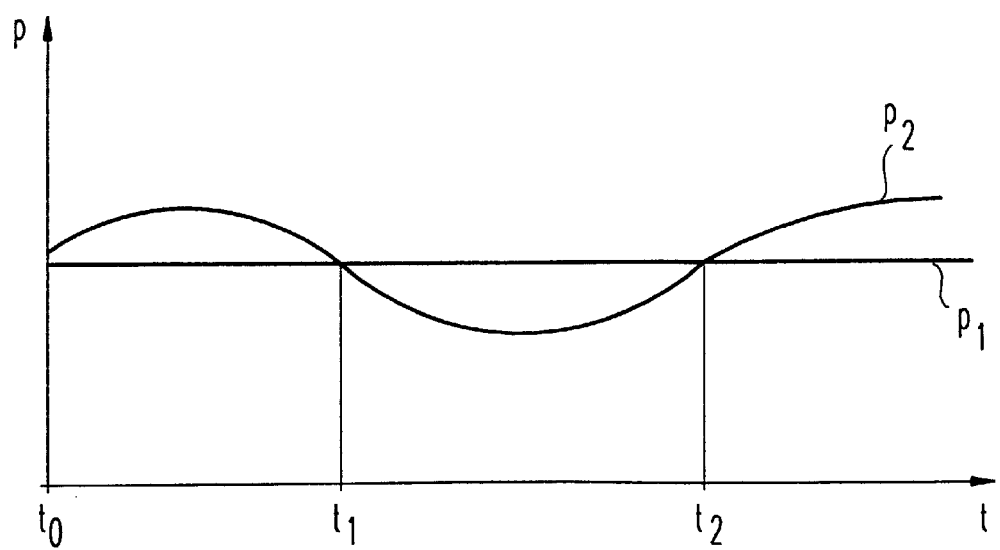
FIG. 5 is a time diagram to explain the action of the arrangement according to FIG. 4.

At the proximal end of the conduit 10, again, a compressed-gas source 16 and a liquid source 17 (under pressure) are connected by way of pipes 19 and 20, respectively. In the pipes 19 and 20 are provided, in addition to the valves 14 and 15 described above, a first check valve 25 and a second check valve 26. The compressed-gas source 17 delivers gas with a first pressure $p_1$, and the liquid source 17 delivers the liquid with a second pressure $p_2$. The time courses of the output pressures $p_1$ and $p_2$ are shown in FIG. 5.

While the pressure $p_2$ of the compressed-gas source 16 oscillates—that is, rises for a time t and falls again—the pressure $p_1$ of the liquid source 17 is substantially constant. The pressure $p_2$ fluctuates about the pressure $p_1$ in such a way that during the period $t_0$ to $t_1$ (in FIG. 5) it is above the pressure $p_1$ and in the period $t_1$ to $t_2$ it is below the pressure $p_1$. After $t_2$ the pressure $p_2$ again rises above the pressure $p_1$. These pressure relationships ensure that during the period $t_1$ to $t_2$ rinsing liquid passes out of the liquid container 17 into the conduit 10, and during the period $t_0$ to $t_1$ or after $t_2$ the slug of liquid that has thus entered the conduit 10 is accelerated along the conduit 10, by gas from the compressed-gas source 16, and expelled from the opening 11. The valves 14 and 15 here act solely to turn the process on and off, whereas it is controlled by the oscillation of the compressed-gas source. Another important feature of this arrangement is that the lengths of the pipes are made such that the individual liquid slugs, as discussed above (in accordance with the selected pressures and amounts of liquid), are expelled from the opening 11 with maximal energy.

It is of course also possible for the pressure $p_1$ of the rinsing liquid not to be kept constant but rather to oscillate 180° out of phase with the pressure $p_2$, or to keep $p_2$ constant and let $p_1$ oscillate.

Another advantage of the invention lies in the fact that either gas or liquid can also be used alone, with no need for separate equipment. Because the valves are situated near the junction A, during the switch from gas to liquid (and the reverse) only a minimal residual amount of the preceding medium is expelled. The flow rates and pressures of the two media are preferably made adjustable within fairly broad ranges, so that a maximal rinsing or cleaning variability is achieved with a single apparatus.

List of reference numerals

10 Conduit
11 Opening
12 Endoscope
13 Slug of liquid
14 First valve
15 Second valve
16 Compressed-gas source
17 Liquid source
18 3-way valve
19 First connecting pipe
20 Second connecting pipe
21 Amplifier
22 Controller
23 First adjustment unit
24 Second adjustment unit
25 First check valve
26 Second check valve

What is claimed is:
1. An apparatus for rinsing an operation field during endoscopy comprising:
an endoscope having a conduit provided with a proximal section and with a distal section which has an outlet opening;

a liquid source in flow communication with the proximal section of the conduit;

a compressed-gas source in flow communication with the proximal section of the conduit;

first and second controllable valves between the proximal section of the conduit and the liquid source and between the proximal section of the conduit and compressed-gas source, respectively, the first and second valves being sequentially open so as to enable a controllable portion of liquid filling part of the proximal portion during opening of the first valve to be driven toward the outlet opening at an accelerating rate by a gas portion introduced into the proximal section upon opening of the second valve after the first valve has been closed.

2. The apparatus of claim 1 wherein the first and second controllable valves comprise check valves which are opened and closed by varying a relative pressure between the liquid source and the compressed gas source.

3. The apparatus of claim 1 wherein the first and second valves are open repeatedly such that a plurality of portions of liquid are created.

4. The apparatus of claim 3 wherein the first and second valves are open at regular intervals such that the plurality of portions of liquid are created at regular intervals.

5. An apparatus for rinsing an operation field during endoscopy comprising:

a conduit provided with a proximal section and with a distal section which has an outlet opening;

a liquid source in flow communication with the proximal section of the conduit;

a compressed-gas source in flow communication with the proximal section of the conduit;

a 3-way controllable valve having first and second inputs in flow communication with the liquid and gas-compressed sources, respectively, and an output in flow communication with the proximal section of the conduit;

a second adjustment unit for adjusting a pulse duration to an amount of liquid portions which are periodically introduced into the proximal section of the conduit from the output of the 3-way controllable valve, each portion of liquid partially filling the conduit; and a first adjustment unit driving the 3-way controllable valve at a frequency for controlling an interval at which subsequent liquid portions are expelled from the outlet opening.

6. The apparatus of claim 5 wherein the first adjustment unit is driving the 3-way controllable valve at a constant frequency such that liquid portions are expelled from the outlet opening at regular intervals.

* * * * *